United States Patent [19]

Albright

[11] 3,972,945

[45] Aug. 3, 1976

[54] PROCESS FOR THE SELECTIVE SYNTHESIS OF SALICYLALDEHYDES

[75] Inventor: Charles F. Albright, Granada Hills, Calif.

[73] Assignee: The Garrett Corporation, Los Angeles, Calif.

[22] Filed: Dec. 23, 1974

[21] Appl. No.: 535,895

[52] U.S. Cl. .................................... 260/600 R
[51] Int. Cl.² ................................. C07C 45/00
[58] Field of Search .................................. 260/600

[56] References Cited
UNITED STATES PATENTS
3,780,110  12/1973  Gay et al. .................... 260/600

OTHER PUBLICATIONS
Ferguson et al., J.A.C.S., vol. 68 (1946), 2502–2504.
Crown Zellerbach Pamphlet – Dimethyl Sulfoxide as a Reaction Solvent, (1968) p. 1.
Du Pont Pamphlet – A Review Of Catalytic & Synth. Appln's. for DMF & DMAC, (1961) p. 1.

Primary Examiner—Bernard Helfin
Attorney, Agent, or Firm—Benton S. Duffett, Jr.; Albert J. Miller

[57] ABSTRACT

The classical Reimer-Tiemann reaction for the synthesis of phenolic aldehydes has been modified from an aqueous to a non-aqueous system to provide an improved route for the formation of salicylaldehydes and, preferably, 3-substituted salicylaldehydes, e.g. 3-fluorosalicylaldehyde. Heretofore, compounds such as 3-substituted salicylaldehydes have proven to be extremely difficult to prepare in other than small laboratory quantities from the corresponding ortho-substituted phenol, since, in the final salicylaldehyde, each position ortho to the hydroxyl group contains substitution. In particular, with respect to 3-fluorosalicylaldehyde, one of the positions is occupied by the strongly electronegative fluorine atom so that the principal reaction product in the aqueous Reimer-Tiemann reaction has always been the para-isomer (3-fluoro-4-hydroxy-benzaldehyde), only negligible quantities of the desired ortho-isomer being obtained. In the process of the present invention, o-fluorophenol is caused to react with sodium hydroxide and chloroform in a hydrocarbon diluent (preferably benzene), maintaining the reaction under essentially anhydrous conditions by taking up the water of reaction with excess sodium hydroxide. It is necessary that an aprotic solvent, such as N,N-dimethylformamide, be employed as a catalyst. The use of boron oxide, while not absolutely necessary to the reaction, has been found to be advantageous in that the reaction proceeds more smoothly if the phenoxyboroxine is formed initially. The boron oxide also acts as a dehydrating agent and aids in removing the water of reaction. The preferential reaction product is the desired 3-fluorosalicylaldehyde, no paraisomer having been found. After hydrolysis and neutralization, the 3-fluorosalicylaldehyde can be recovered by azeotropic distillation along with a substantial quantity of unreacted o-fluorophenol which can be purified for recycle in subsequent preparations.

26 Claims, No Drawings

PROCESS FOR THE SELECTIVE SYNTHESIS OF SALICYLALDEHYDES

BACKGROUND OF THE INVENTION

Heretofore, there has been a need for an efficient process for the production of 3-fluorosalicylaldehyde which is necessary to the preparation of fluomine [cobalt bis (3-fluorosalicylaldehyde)-ethylenediimine], useful for the chelation of oxygen in aerospace applications. 3-Fluorosalicylaldehyde has proven to be extremely difficult to prepare in more than small laboratory quantitites in the past since each position ortho to the ring hydroxyl group is substituted. The presence of the strongly electronegative fluorine atom which blocks one of the ortho positions tends to deactivate the remaining ortho position so that the para-isomer (3-fluoro-4-hydroxybenzaldehyde) is formed preferentially. Prior processes for the preparation of 3-fluorosalicylaldehyde have tended to be highly time-consuming and are characterized by low overall yields.

The only practical starting material for the preparation of 3-fluorosalicylaldehyde is ortho-fluorophenol, although a seven step process starting with 2-amino-4-chloroanisole has been reported (U.S. Pat. Nos. 2,576,064; 2,576,065; 2,590,813; and 2,676,189.

The direct preparation using the conventional Reimer-Tiemann reaction for the synthesis of salicylaldehydes, although having the advantage of extreme simplicity, has not proven to be practical since yields of the ortho-isomer were generally less than 7 percent, the bulk of the phenol having been converted to the para-isomer. It should be noted that the conventional Reimer-Tiemann reaction is conducted in an aqueous system.

The Kolbe-Schmidt reaction, involving the carboxylation of an alkali salt of o-fluorophenol with carbon dioxide under pressure, gives both the ortho and para-isomers of the acid. The mixture of acids can be reduced by sodium amalgam to the corresponding aldehydes, separation of the aldehydes then being effected by azeotropic distillation of the desired 3-fluorosalicylaldehyde. It is necessary to use a primary amine such as p-toluidine to stop the reduction at the aldehyde stage and prevent further reduction to the alcohol. This procedure was utilized by Melvin Calvin and his coworkers at the University of California at Berkeley for the initial bulk preparations of 3-fluorosalicylaldehyde during the 1940's (see U.S. Pat. No. 2,493,654).

The initial preparation of 3-fluorosalicylalcohol, followed by subsequent oxidation to the desired 3-fluorosalicylaldehyde, has also been reported (U.S. Pat. No. 3,780,110). This involves the reaction of o-fluorophenol with trioxane utilizing the technique disclosed by Marchand and Grenet (U.S. Pat. No. 3,290,393) in which the phenoxyboroxine is prepared initially so as to reduce resin formation. This synthesis also requires the use of p-toluidine (or other primary amine) during the oxidation so as to stop the oxidation at the aldehyde stage.

Both the acid and alcohol routes are time consuming, result in relatively low overall yields, and require involved purification steps since it is necessary to eliminate all traces of p-toluidine from the 3-fluorosalicylaldehyde, such primary amines having been found to deactivate the fluomine which is the desired final product.

It has now been found that the Reimer-Tiemann reaction will take place in hydrocarbon diluents under essentially anhydrous conditions if the reaction is catalyzed by an aprotic solvent such as N,N-dimethylformamide. A completely anhydrous reaction is not possible since water forms during the reaction but this can be effectively removed by the use of excess sodium hydroxide (solid). Using the anhydrous Reimer-Tiemann process, yields of 12.5 to 15 percent have been consistently obtained even when scaled-up. Recovery and recycle of unreacted phenol indicates overall yields should approach 50%. The simiplicity and rapidity of the conventional Reimer-Tiemann synthesis is maintained, with the exception that an extraction step is required.

In additon, an improved method for separation of the unreacted o-fluorophenol from the desired 3-fluorosalicylaldehyde has been developed so that the overall manufacturing time is completely minimized. No primary amines are required during the recovery phase so that no possible contamination of the final product is possible. The only by-products found have been a minimal quantity of black tar (soluble in acetone) and a white powder (m.p. in excess of 170°C) which azeotropes with difficulty during the distillation stage. It has been determined that this white powder does not affect the activity of fluomine. The process seems to be selective for formation of the ortho-isomer (salicylaldehyde) since no para-isomer has been found.

It is an object of the present invention to provide an improved process for the synthesis of salicylaldehydes from phenolic starting materials.

It is an object of the present invention to provide an improved process for the direct preparation of 3-substituted salicyladehydes (e.g. 3-fluorosaliclaldehyde), using the reactants and simplicity inherent in the classical Reimer-Tiemann synthesis, by modification of this synthesis so that the reaction takes place under essentially anhydrous conditions, the water of reaction being taken up by an excess of sodium hydroxide or other dehydrating agent. The reaction proceeds in a hydrocarbon diluent such as benzene when it is catalyzed by a solvent such as N,N-dimethylformamide.

It is a further object of the present invention to provide a process for the preparation of 3-fluorosalicylaldehyde on a more efficient basis and in greater overall yield than, heretofore, generally was possible in the prior art.

It is an object of the present invention to provide an improved route for the direct preparation of 3-fluorosalicylaldehyde with minimum formation of the unwanted para-isomer and other undersirable by-products and tars.

It is another object of the present invention to provide an improved process for the expeditious synthesis of 3-fluorosalicylaldehyde wherein the overall reaction and recovery time is accelerated when compared with processes of the prior art.

It is an object of the present invention to provide an improved method for recovery and purification of the desired 3-fluorosalicylaldehyde from the reaction step.

It is an object of the present invention to provide an improved route for the production, recovery and purification of 3-fluorosalicylaldehyde in the absence of any chemical agents (such as p-toluidine) which could subsequently contaminate and deactivate the fluomine prepared therefrom.

It is another object of the present invention to provide an improved process for the synthesis of 3-fluorosalicylaldehyde which is amenable to large scale implementation.

These and other objects, as well as the scope, nature and utilization of the process, will be apparent from the following detailed description and appended claims.

SUMMARY OF THE INVENTION

It has been found that an improved process for the preferential preparation of a salicylaldehyde with negligible formation of the corresponding 4- hydroxybenzaldehyde (para-isomer) comprises reacting a phenol with an alkali metal hydroxide and chloroform, said reaction being carried out with agitation at elevated temperatures of about 50° to 150°C under reflux conditions in a substantially non-aqueous reaction zone, the water of reaction being removed by formation of a concentrated alkali metal hydroxide solution, the reaction being carried out in a hydrocarbon diluent and catalyzed by an effective concentration of a catalyst selected from the group consisting essentially of N,N-dimethlformamide, N,N-dimethylacetamide, and dimethyl sulfoxide.

DESCRIPTION OF PREFERRED EMBODIMENTS

It has been found in a preferred embodiment that a process for the direct preparation of 3-fluorosalicylaldehyde from o-fluorophenol comprises:

a. reacting o-fluorophenol with sodium hydroxide and chloroform in a substantially non-aqueous reaction zone, utilizing a hydrocarbon (benzene) as a diluent, and a catalytically effective concentration of a catalyst selected from the group consisting essentially of N, N-dimethylformamide, N,N-dimethylacetamide and dimethyl sulfoxide, the water of reaction being removed by an excess of sodium hydroxide or by the use of other dehydrating agents such as boric oxide. This is the classical Reimer-Tiemann reaction for the preparation of salicylaldehydes conducted under anhydrous conditions.

(or) the initial reaction of o-fluorophenol with boric oxide to form the o-fluorophenoxyboroxine which then replaces o-fluorophenol in the above reaction. The reaction proceeds somewhat more smoothly when the phenoxyboroxine is employed. Since the boric oxide takes up part of the water of reaction, not so much excess sodium hydroxide is required.

b. hydrolysis of the reaction mix in the cold (10°C or less), followed by separation of the basified aqueous layer from the hydrocarbon. The aqueous solution is acidified and subjected to azeotropic distillation to remove the desired 3-fluorosalicylaldehyde and unreacted o-fluorophenol. The two distill together and separate as an 'oil', heavier than water. The aldehyde can be recovered from the phenol by adding sufficient water to dissolve the o-fluorophenol (which is relatively soluble) and chilling the water-oil mixture to 5°C or less which results in precipitation of the pure 3-fluorosalicylaldehyde.

In the discussion of the anhydrous Reimer-Tiemann process, the use of o-fluorophenol in the synthesis of 3-fluorosalicylaldehyde has been stressed. It should not be construed, however, that this anhydrous process is limited to this single compound or to the formation of 3-substituted salicylaldehydes. The anhydrous Reimer-Tiemann reaction being disclosed has a general application to the selective preparation of the salicylaldehydes from phenol and substituted phenols in which the substituent may be other than a fluorine atom and/or attached to the ring in other than the ortho position. It is, of course, necessary that an ortho position be available for attachment of the formyl group during the reaction. The term 'orthofluorophenol' or 'o-fluorophenol' is also intended to include any substituted orthofluorophenols in which the substituent is on the ring in a position other than the remaining available ortho position. In a preferred embodiment of the process 3-substituted salicylaldehydes are produced from ortho-substituted phenols. Exemplary 3-substituted salicylaldehydes, other than 3-fluorosalicylaldehyde, which may be formed by the process of the present invention include 3-chlorosalicylaldehyde, 3.5-difluorosalicyladehyde, 3.5-dichlorosalicylaldehyde, 3-methoxysalicylaldehyde, 3-ethoxysalicylaldehyde, 3-methylsalicylaldehyde, etc.

The ortho-fluorophenol (liquid having a density of 1.26, m.w. 112.1, b.p. 151°-152°C), required as a starting material for the preparation of 3-fluorosalicylaldehyde, is commercially available. It should preferentially be chemically pure and free of water (anhydrous). If necessary it can be dried by azeotropic distillation with suitable hydrocarbon.

Boron oxide ($B_2O_3$) is sometimes identified as boric oxide or boric anhydride.

The preferred catalyst is N,N-dimethylformamide which exhibits the formula $HCON(CH_3)_2$ and is sometimes identified as DMF. Other aprotic solvents, such as dimethylacetamide or dimethyl sulfoxide, may also prove suitable. The catalyst selected should also be freed of water before use. In the absence of a catalyst of this type the desired reaction is extremely slow.

The hydrocarbon diluents, required to keep the reaction mix in a fluidized state, do not enter into the chemical reactions. They are preferably aromatic in nature, e.g. benzene, toluene, xylene, ethyl benzene, isopropyl benzene, etc. Aliphatic hydrocarbons such as hexane and petroleum ethers alternatively may be selected. The particularly preferred hydrocarbon diluent is benzene since its boiling point (80°) is such that the reaction can be kept at a suitably high temperature while at the same time the heat of reaction can be removed by reflux of the hydrocarbon.

The reaction is the classical Reimer-Tiemann synthesis for the direct preparation of salicylaldehydes from phenols which has, heretofore, always been carried out in aqueous solutions. The key point in this invention is the modification of the Reimer-Tiemann synthesis so that it is carried out under substantially non-aqueous conditions, the principal product of the reaction then being the desired ortho-isomer. Since ion-exchange is involved, it is necessary that the aprotic solvent (DMF) be employed as a catalyst. In its simplest form the Reimer-Tiemann reaction consists of adding chloroform $CHCl_3$) to a stirred, aqueous solution of the sodium phenoxide, maintaining the reaction temperature at about 50°–60°C. The reaction can be written as:

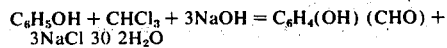

$C_6H_5OH + CHCl_3 + 3NaOH = C_6H_4(OH)(CHO) + 3NaCl\ 30\ 2H_2O$

It is evident from the equation that water is formed during the reaction so that completely anhydrous conditions cannot be met. It is possible, however, to take up the water of reaction with excess sodium hydroxide which effectively acts as a dehydrating agent as the reaction proceeds. The amount of excess sodium hydroxide employed was generally 1 to 1½ moles for each mole of water which would be expected to form on a theoretical basis if the reaction went to completion. If the phenoxyboroxine was formed initially, by the reaction of the phenol with boron oxide (preferentially 1 mole phenol for each mole of $B_2O_3$), the lower figure (1 mole of excess NaOH per mole of liberated water) was used since a portion of the expected water was taken up by the formation of metaboric acid $(HOBO)_3$. Since neither the solid sodium hydroxide nor the boron oxides are soluble in the hydrocarbon, the reaction mix is a slurry which must be kept suspended by rapid agitation.

Considerable leeway is permitted as to the quantities of reactants which can be successfully employed. The initial preparation of the phenoxyboroxine is advantageous in that esterification of the phenol with boron reduces possible polymerization on the hydroxyl group, thereby reducing by-product and tar formation and leaving more unreacted o-fluorophenol available for recycle. When the phenol was reacted directly, however, no significant decrease was found in the yield of 3-fluorosalicylaldehyde obtained, so initial esterification with boron is not mandatory. It was found, however, that the reaction proceeds more smoothly with the phenoxyboroxine. The fact that the boron oxide also has the ability to remove a portion of the water of reaction and maintain the desired anhydrous conditions led to its continued use on a preferential basis. Since it can be completely eliminated the quantity employed may be varied but from a practical standpoint it was found that about 0.75 to 1.25 moles per mole of o-fluorophenol was adequate.

The quantity of catalyst employed may be varied. The reaction will proceed with as little as 5 cc DMF per mole of o-fluorophenol, although at a somewhat slower rate. Preferentially about 60 cc DMF were used per mole of o-fluorophenol, 20 cc being added before the phenoxyboroxine was formed, the remainder being added as a mixture with chloroform and benzene during the reaction. With the quantity the reaction will proceed at a vigorous rate. The highly alkaline conditions catalyze hydrolysis of the DMF to dimethylamine and formic acid so that a small portion of the DMF is destroyed during the reaction. Whether the DMF enters into the reaction and forms by-products and/or contributes to tar formation is not known. No attempt was made to recover the catalyst although this may be economical on a larger scale.

Solid sodium hydroxide was added in pellet form although a flake form may also be employed. It would be expected that other alkali metal hydroxides may also prove practical. If the phenoxyboroxine was formed initially, 5 moles of NaOH per mole of o-fluorophenol was used, whereas 6 moles were employed if boron oxide was eliminated. If the reaction were to go to completion the resulting sodium hydroxide solution would be about 60% or better. However, since the reaction never went to completion a considerable quantity of solid NaOH remained and it is probable that the quantity of sodium hydroxide could be reduced to the stoichiometric amount (3 moles per mole of o-fluorophenol) without detriment.

For the bulk of the preparations an excess of chloroform (1.25 times theory) was used. The preferred quantity of chloroform, however, was determined to be less than the theoretical mole per mole of o-fluorophenol since the formation of by-products and tars is suppressed making more unreacted o-fluorophenol available for recovery and recycle while there is no significant effect on the yield. For example, the recovered yield of 3-fluorosalicylaldehyde was not appreciably altered when the quantity of chloroform was reduced to 75% of theory. When the quantity was dropped to 37.5% of theory, however, practically no 3-fluorosalicylaldehyde was recovered. For comparative purposes the yield is always based on the quantity of o-fluorophenol used in the reaction.

The preferred hydrocarbon diluent is benzene since the heat of reaction can be removed by reflux and the reaction temperature can be readily maintained at the reflux temperature of about 80°C. The reaction, however, is not limited to this temperature, since variation of the reaction temperature provides a method for optimization of the overall yield. The desired reaction temperature can be obtained by selection of an appropriate hydrocarbon or by subjecting the reaction to pressure. The quantity of hydrocarbon required is that which is sufficient to fluidize the slurry. In laboratory reactions this was found to be about 1200 cc of benzene per mole of o-fluorophenol reacted. Some hydrocarbon was also used in the chloroform-dimethylformamide mixture so as to achieve better control of the addition rate.

The chloroform is added to the reaction mixture consisting of the o-fluorophenol (or o-fluorophenoxyboroxine), solid sodium hydroxide, and dimethylformamide (catalyst) in the hydrocarbon diluent (benzene) during about a 30 to 60 minute period. Since better control could be achieved when the volume of the additive (chloroform) was increased, the preferred method was to use a mixture of the chloroform (0.75 to 1.25% of theory), catalyst (DMF, 40 cc), and benzene (100 cc), the total volume being 200 cc or better. The reaction proceeds vigorously with reflux since considerable heat of reaction is evolved. Additional heating or cooling was applied as necessary to maintain the reaction temperature at reflux (78° to 80°C). After addition of all of the chloroform, the reaction mix was maintained at reflux (applying heat as required) for an additional 30 to 60 minutes for a total reaction time of 1 to 2 hours. The reaction mix temperature gradually drops to about 76°C during this period. The time required to add the chloroform to the reaction, or for the subsequent reaction after addition of the chloroform, is not critical and can be varied within wide limits from that given above. Optimization would be on the basis of by-product formation and the quantity of unreacted o-fluorophenol which could be recovered for recycle.

Upon completion of the reaction, the reaction mix is cooled to below 10°C and then hydrolyzed with cold (5°C) water (about 1500 cc/mole of o-fluorophenol). Hydrolysis in the reactor is preferred since the reaction mix is a sludge which can set up rapidly if agitation is not maintained. The basified aqueous solution (dark green to black) is separated from the hydrocarbon (which is further extracted with basic solutions), and acidified (pH about 2), whereupon a brown to black oil will settle out. The combined oil and water is subjected to azeotropic distillation. Since 3-fluorosalicylaldehyde can solidify in the condenser if sufficiently pure, it is preferential to use a condenser which can be rodded out. Initially a benzene-water azeotrope distills off (70° to 95°C), followed by a combined azeotrope of unreacted o-fluorophenol, 3-fluorosalicylaldehyde, and water (96° to 100°C). The combined o-fluorophenol and 3-fluorosalicylaldehyde, which constitute the organic portion of the azeotrope, will separate from the distillate as an 'oil' which is heavier than water. The o-fluorophenol, being more soluble in water (estimated solubility is 4 to 5 percent at room temperature) can be separated from the relatively insoluble 3-fluorosalicylaldehyde by washing the 'oil' with sufficient cold water. The laboratory procedure consists of increasing the volume of water to about 2000 cc, swirling the oil in the water, and chilling the combined 'oil' and water to below 5°C, whereupon the 'oil' solidifies into pure 3-fluorosalicylaldehyde which can be filtered and washed with additional cold water to remove any entrained o-fluorophenol. On a large scale the azeotrope could be distilled directly into a receiver containing deionized water which had been refrigerated to below 10°C and which was agitated so as to facilitate separation and crystallization of the desired 3-fluorosalicylaldehyde. The filtered 3-fluorosalicylaldehyde (after washing) can be air-dried but since the vapor pressure is relatively high, significant losses can occur through evaporation. Final drying should be over a dessicant.

The optimum recovery and purification procedures may vary from salicylaldehydes other than 3-fluorosalicylaldehyde as will be apparent to those skilled in the art. For example, in some instances it may be desirable to effect separation of the unreacted phenol from the salicylaldehyde product through the bisulfite-addition product.

The synthesis is carried out in a reaction vessel of sufficient size so that hydrolysis of the reaction mix can preferentially be effected in the same vessel. It should be provided with a method for both heating and cooling, with agitation powerful enough to keep the reaction solids fluidized and in suspension (a heavy sludge is formed near the end of the reaction), and with a condenser having sufficient cooling capacity to handle a rapid boil-up of benzene.

EXAMPLE

The following example illustrates the process of this invention but it should be understood that the invention is not limited to the specific details set forth.

Anhydrous o-fluorophenol (112 gm, 1 mole), powered boric anhydride ($B_2O_3$, 70 gm, 1 mole) and anhydrous dimenthylformamide (20 cc) were mixed in a reactor (10 liter capacity), with benzene (1200 cc). The mixture was refluxed at 80° to 82°C for one hour with agitation to maintain the powdered boric anhydride in suspension. A slightly milky solution resulted with some precipitated white, somewhat gummy, solid (probably metaboric acid). The reflux was two phases (benzene-water azeotrope) but no water was removed. The solution was then cooled to about 50°C and sodium hydroxide pellets (200 gm, 5 mole) were added. These were maintained in suspension with rapid agitation and the mixture was reheated to reflux. A homogenous solution (240 cc) containing chloroform (100 cc, 1.25 moles), dimethylformamide (40 cc) and benzene (100 cc) was then added slowly during a 45 minute period (about 5cc/min.), meanwhile maintaining the reaction mix at reflux. The pellets of sodium hydroxide gradually disappeared and a thick sludge was obtained with the color changing from ivory to yellow to orange to brown by the end of the reaction. The reaction was then continued at reflux (with heat input as required) for an additional 55 minutes after all the chloroform solution had been added, for a total reaction time of about 100 minutes. The reaction mix was then cooled, hydrolyzed in the reactor, and the basic aqueous solution was separated and removed to a distillation flask where it was neutralized with hydrochloric acid (about 350 cc of concentrated 36 percent HCl) to a definite pH of less than 2.0. The dimethylformamide forms a hydrogen chloride complex and consumes a portion of the acid. Azeotropic distillation followed by crystallization, filtration, and drying, resulted in 17.5 grams (12.5% of theory) of pure 3-fluorosalicylaldehyde (m.w. 140.11, m.p. 68°–69°C) being recovered. The volume of oil which separated from the azeotrope indicated that about 40 to 60 percent of the o-fluorophenol had not reacted and could be recovered for recycle. A black tar (insoluble in acetone) remained in the distillation flask but no para-isomer was detected.

It is within the scope of this invention to expand the reaction which takes place in the Reimer-Tiemann synthesis for the direct preparation of phenolicaldehydes, and which has, heretofore, been conducted only in aqueous solutions, into non-aqueous mediums, thereby making it possible to selectively prepare the salicylaldehyde in the substantial absence of the para-isomer. The simplicity and rapidity of the normal Reimer-Tiemann reaction is maintained. Although the invention has been described with preferred embodiments, it is understood that variations and modifications may be required as will be apparent to those skilled in the art. Such variations or modifications are to be considered within the purview and scope of the claims appended hereto.

I claim:

1. A process for the preferential preparation of a salicylaldehyde with negligible formation of the corresponding 4-hydroxybenzaldehyde comprising reacting a phenol with an alkali metal hydroxide and chloroform, said reaction being carried out with agitation at elevated temperatures of about 50° to 150°C., under reflux conditions in a substantially non-aqueous reaction zone, the water of reaction being removed by formation of a concentrated alkali metal hydroxide solution upon reaction with excess alkali metal hydroxide, the reaction being carried out in a hydrocarbon diluent and catalyzed by an effective concentration of a catalyst selected from the group consisting essentially of N,N-dimethylformamide, N,N-dimethylacetamide, and dimethyl sulfoxide.

2. A process according to claim 1 wherein said phenol is initially reacted with boron oxide to form the phenoxyboroxine which is then further reacted with the alkali metal hydroxide and chloroform using the conditions set forth in claim 1.

3. A process whereby the salicylaldehyde, prepared in the manner as set forth in claim 2, is recovered from the reaction mix by hydrolysis of the reaction mix with water, separation of the basic aqueous solution containing the salts of the unreacted phenol and salicylaldehyde from the hydrocarbon, extraction of the hydrocarbon with addditional basified water, acidification of the combined water extracts, followed by distillation to recover the salicylaldehyde and unreacted phenol.

4. A process according to claim 1 wherein said catalyst is N,N-dimethylformamide.

5. A process according to claim 1 wherein said alkali metal hydroxide is sodium hydroxide.

6. A process according to claim 1 wherein the water of reaction is effectively removed by the use of an excess of sodium hydroxide, the quantity of sodium hydroxide being increased from a theoretical 3 to as much as 6 or more moles per mole of said phenol.

7. A process according to claim 1 wherein the water of reaction is effectively removed in part by the use of boron oxide which forms hydrates.

8. A process according to claim 1 wherein the hydrocarbon diluent is an aromatic hydrocarbon.

9. A process according to claim 1 wherein the said hydrocarbon diluent is benzene and the reaction is carried out at a reflux temperature of about 80°–82°C.

10. A process according to claim 1 wherein the said hydrocarbon diluent is present in a weight concentration which exceeds the quantity of said phenol charged by about 5 to 25 times.

11. A process according to claim 1 wherein the chloroform is added to the reaction mix over a period of from about 0.25 to 6 hours and further reacted for 0 to 6 hours.

12. A process for the preferential preparation of a 3-substituted salicylaldehyde with negligible formation of the corresponding 4-hydroxybenzaldehyde comprising reacting an orthosubstituted phenol with an alkali metal hydroxide and chloroform, said reaction being carried out with agitation at elevated temperatures of about 50 to 150°C., under reflux conditions in a substantially non-aqueous reaction zone, the water of reaction being removed by formation of a concentrated alkali metal hydroxide solution upon reaction with excess alkali metal hydroxide, the reaction being carried out in a hydrocarbon diluent and catalyzed by an effective concentration of a catalyst selected from the group consisting essentially of N,N-dimethylformamide, N,N-dimethylacetamide, and dimethyl sulfoxide.

13. A process according to claim 12 wherein said orthosubstituted phenol is initially reacted with boron oxide to form the phenoxyboroxine which is then further reacted with the alkali metal hydroxide and chloroform using the conditions set forth in claim 12.

14. A process whereby the 3-substituted salicylaldehyde, prepared in the manner as set forth in claim 13, is recovered from the reaction mix by hydrolysis of the reaction mix with water, separation of the basic aqueous solution containing the salts of the unreacted ortho-substituted phenol and 3-substituted salicylaldehyde from the hydrocarbon, extraction of the hydrocarbon with additional basified water, acidification of the combined water extracts, followed by distillation to recover the 3-substituted salicylaldehyde and unreacted ortho-substituted phenol.

15. A process according to claim 12, wherein the said ortho-substituted phenol is o-fluorophenol and the said 3-substituted salicylaldehyde is 3 -fluorosalicylaldehyde.

16. A process wherein the 3-substituted salicylaldehyde recovered using the procedure detailed in claim 14 is 3-fluorosalicylaldehyde which can be separated from unreacted o-fluorophenol by the addition of sufficient cold water to dissolve the o-fluorophenol, whereupon the 3-fluorosalicylaldehyde will solidify and precipitate from solution.

17. A process according to claim 12 wherein said catalyst is N,N-dimethylformamide.

18. A process according to claim 12 wherein said alkali metal hydroxide is sodium hydroxide.

19. A process according to claim 12 wherein the water of reaction is effectively removed by the use of an excess of sodium hydroxide, the quantity of sodium hydroxide being increased from a theoretical 3 to as much as 6 or more moles per mole of said ortho-substituted phenol.

20. A process according to claim 12 wherein the water of reaction is effectively removed in part by the use of boron oxide which forms hydrates.

21. A process according to claim 15 wherein about 0.50 to 1.50 mole of chloroform is provided per mole of o-fluorophenol charged.

22. A process according to claim 15 wherein the catalyst is present in a concentration of about 5 to 50 percent by weight based on the weight of o-fluorophenol charged.

23. A process according to claim 12 wherein the hydrocarbon diluent is an aromatic hydrocarbon.

24. A process according to claim 12 wherein the said hydrocarbon diluent is benzene and the reaction is carried out at a reflux temperature of about 80°–82°C.

25. A process according to claim 12 wherein the said hydrocarbon diluent is present in a weight concentration which exceeds the quantity of said ortho-substituted phenol charged by about 5 to 25 times.

26. A process according to claim 12 wherein the chloroform is added to the reaction mix over a period of from about 0.25 to 6 hours and further reacted for 0 to 6 hours.

* * * * *

UNITED STATES PATENT AND TRADEMARK OFFICE
CERTIFICATE OF CORRECTION

PATENT NO. : 3,972,945
DATED : August 3, 1976
INVENTOR(S) : Charles F. Albright

It is certified that error appears in the above—identified patent and that said Letters Patent are hereby corrected as shown below:

Column 4, line 57, change "$CHCl_3$)" to --($CHCl_3$)--

Column 4, lines 61-63, change the reaction to read
--$C_6H_5OH + CHCl_3 + 3NaOH = C_6H_4(OH)(CHO) + 3NaCl + 2H_2O$--

Column 7, line 26, change "from" to --for--

Signed and Sealed this

Twelfth Day of October 1976

[SEAL]

*Attest:*

RUTH C. MASON
*Attesting Officer*

C. MARSHALL DANN
*Commissioner of Patents and Trademarks*